(12) United States Patent
Rohaly et al.

(10) Patent No.: US 7,497,991 B2
(45) Date of Patent: Mar. 3, 2009

(54) REAGENT TUBE FOR TOP LOADING ANALYZER

(75) Inventors: Steven J. Rohaly, Benton Harbor, MI (US); Joel C. Mitchell, Bridgman, MI (US)

(73) Assignee: Leco Corporation, St. Joseph, MI (US)

( * ) Notice: Subject to any disclaimer, the term of this patent is extended or adjusted under 35 U.S.C. 154(b) by 317 days.

(21) Appl. No.: 11/338,171

(22) Filed: Jan. 24, 2006

(65) Prior Publication Data

US 2007/0172391 A1 Jul. 26, 2007

(51) Int. Cl.
G01N 31/12 (2006.01)
(52) U.S. Cl. ......................................................... 422/78
(58) Field of Classification Search .................... 422/78
See application file for complete search history.

(56) References Cited

U.S. PATENT DOCUMENTS

| 4,525,328 A | 6/1985 | Bredeweg |
| 4,622,009 A | 11/1986 | Bredeweg |
| 2004/0171165 A1 | 9/2004 | Mitchell et al. |

*Primary Examiner*—Walter D Griffin
*Assistant Examiner*—Bobby Ramdhanie
(74) *Attorney, Agent, or Firm*—Price, Heneveld, Cooper, DeWitt & Litton, LLP

(57) ABSTRACT

A reagent assembly for a combustion tube includes a reagent tube which is sealably and removably coupled to the open end of the combustion tube such that, when the reagent in the reagent tube is depleted, it can be easily removed without disassembly of the furnace or changing the combustion tube. The reagent tube includes a twist-lock cap to facilitate removal of the reagent tube.

20 Claims, 5 Drawing Sheets

REAGENT TUBE FOR TOP LOADING ANALYZER

BACKGROUND OF THE INVENTION

The present invention relates to elemental analyzers and particularly an analyzer which employs a reagent assembly which is easily removable from the combustion chamber.

A determination of concentration of elements, such as carbon, hydrogen, sulfur, and nitrogen, in an organic sample is desirable for a variety of reasons. In recent years, the food market in particular has become interested in determining the amount of protein in an organic sample, which can be determined by the nitrogen content. Further, the sulfur content, as well as the carbon-to-hydrogen ratio, is desirable in the characterization of coal and coke samples, as are the carbon, hydrogen, and nitrogen ratios in a variety of other organic materials.

Elemental analyzers are commercially available from the Assignee of the present application, Leco Corporation of St. Joseph, Mich., which manufactures CHN analyzers, which are sold under the trademark TRUSPEC®. The analyzer may employ a variable volume ballast chamber of the type disclosed in U.S. Published Application 2004/0171165 A1 (now U.S. Pat. No. 7,070,738, the disclosure of which is incorporated herein by reference. The analyzer disclosed in this published application generally is used for the macro analysis of samples of from about 0.25 grams in size. The combustion system in such an analyzer uses a generally U-shaped quartz combustion tube of the type also disclosed in U.S. Pat. No. 4,622,009, the disclosure of which is incorporated herein by reference. The combustion tube includes a first vertically extending leg which receives a crucible for combustion of a sample and a second vertically extending leg downstream coupled to the first leg and which includes reagents that can serve several purposes. These include scrubbing undesirable products of combustion, enhancing the complete combustion of difficult samples, and/or the removal of excess reagents, such as oxygen. The selection of the reagent is dependent upon the characteristics of the application.

Generally, the analysis of elemental carbon, hydrogen, sulfur, and nitrogen is well known and is discussed in several references, including *Methods in Microanalysis*, Vol. 1, Mirra Osipovna Korshun, 1964, *Instrumental Organic Elemental Analysis*, R. Belcher, 1977; and *Organic Elemental Analysis Ultramicro, Micro, and Trace Methods*, Wolfgang J. Kirsten, 1983. U.S. Pat. No. 4,525,328 discloses an analyzer employing a fixed volume ballast chamber, which collects analytes in an approximately 4.5 L chamber for subsequent analysis. The amount of combustion oxygen used in filling the fixed ballast chamber is significant, and an analysis takes a significant amount of time for the combustion and ballast chamber filling. Also, the byproducts of combustion, i.e., the analyte gases, are somewhat diluted in the relatively large volume ballast chamber. The 2004/0171165 A1 application discloses a variable volume ballast chamber with a movable piston and a combustion detector, such that, during combustion of a sample, the chamber is only filled with byproducts of combustion until the completion of combustion is determined by the combustion detector. Typically, a significantly smaller volume than that of the fixed volume ballast chamber is captured in a more concentrated form of analyte which subsequently can be ejected from the variable volume ballast chamber by controlling a movable piston.

With the variable volume ballast chamber system disclosed in the above-identified published patent application, a large or macro analysis sized sample of 0.10 grams or more are employed. It is desired to provide an analyzer which utilizes a smaller samples, if possible, and conduct an analysis on-the-fly (i.e., detection of the sample during the combustion event as opposed to storing a combustion sample and providing an aliquot sample from a ballast chamber). One difficulty with an on-the-fly analysis system is that, for such micro analysis utilizing a helium carrier gas, an influx plug of excess oxygen is employed to fully combust the sample, and the remaining oxygen must be eliminated prior to detection by flowing the gaseous byproducts of combustion through a reduction reagent, such as copper wire strips.

In the U-shaped combustion tubes used in analyzers, such reagents are packed in the downstream leg of the U-shaped combustion tube and it is necessary after several analyses, which can be anywhere from less than 100 to about 1000 samples, to remove the fused and contaminated reduction reagent from the combustion tube and replace it with new reagents. This requires complete disassembly of the furnace and frequently replacement of the combustion tube itself inasmuch as the reagent packed in the quartz tube tends to melt and stick as a plug in the combustion tube itself. Since combustion takes place at a temperature of nearly 1000° C., this requires considerable time, expense, and manpower, since the furnace must first be cooled, opened, the combustion tube disassembled, and frequently a new combustion tube with a new reagent installed.

Thus, there exists a need for an improved system which allows for on-the-fly micro analysis, i.e. 2 mg to 10 mg samples, utilizing a combustion system which allows for the easy replacement of the reducing reagent.

SUMMARY OF THE INVENTION

The system of the present invention satisfies this need by providing a reagent assembly for a combustion furnace having a combustion tube. The reagent assembly employs a reagent tube which is packed with a reagent and is concentrically positioned in the combustion tube. The reagent tube is sealably and removably coupled to an open end of the combustion tube such that, when the reagent is depleted, the reagent tube can be easily removed without disassembly of the furnace or changing the combustion tube.

In one embodiment of the invention, the reagent tube is top loaded into one leg of a U-shaped combustion tube. In another embodiment, in order to reduce dead volume in the combustion flow path, the reagent tube is inserted into a second tube having an inner diameter greater than the outer diameter of the reagent tube such that a flow path exists between the annular space between the outer wall of the reagent tube and the inner wall of the second tube. The second tube is generally cylindrical and has a closed floor at one end and is inserted into the leg of the combustion tube with the outer diameter of the second tube having a diameter smaller than the inner diameter of the combustion tube. The reagent and second tubes are sealably mounted to the combustion tube such that byproducts of combustion are forced in a tortious flow path, which includes the concentric space between the combustion tube and the outer surface of the second tube then between the space between the inner surface of the second tube and the outer surface of the reagent tube and subsequently upwardly through the open end of the reagent tube to an exit port.

In all embodiments, the reagent tube is packed with reagents and is coupled to a fitting which is easily removed from the combustion furnace and combustion tube and which allows the reagent tube containing an exhausted reagent to be removed from the top of the combustion tube, thereby eliminating the need to remove and/or replace the entire combustion tube from the furnace once the reagent has been expended. In a preferred embodiment of the invention, the fitting includes a twist-lock cap associated with the reagent tube to facilitate its removal. Such a system thereby allows for on-the-fly micro analysis of a sample which utilizes a reagent to remove the excess oxygen and allows the reagent to be replenished as necessary without the time and effort required by existing systems.

These and other features, objects and advantages of the present invention will become apparent upon reading the following description thereof together with reference to the accompanying drawings.

DETAILED DESCRIPTION OF THE PREFERRED EMBODIMENT

Figure 1:
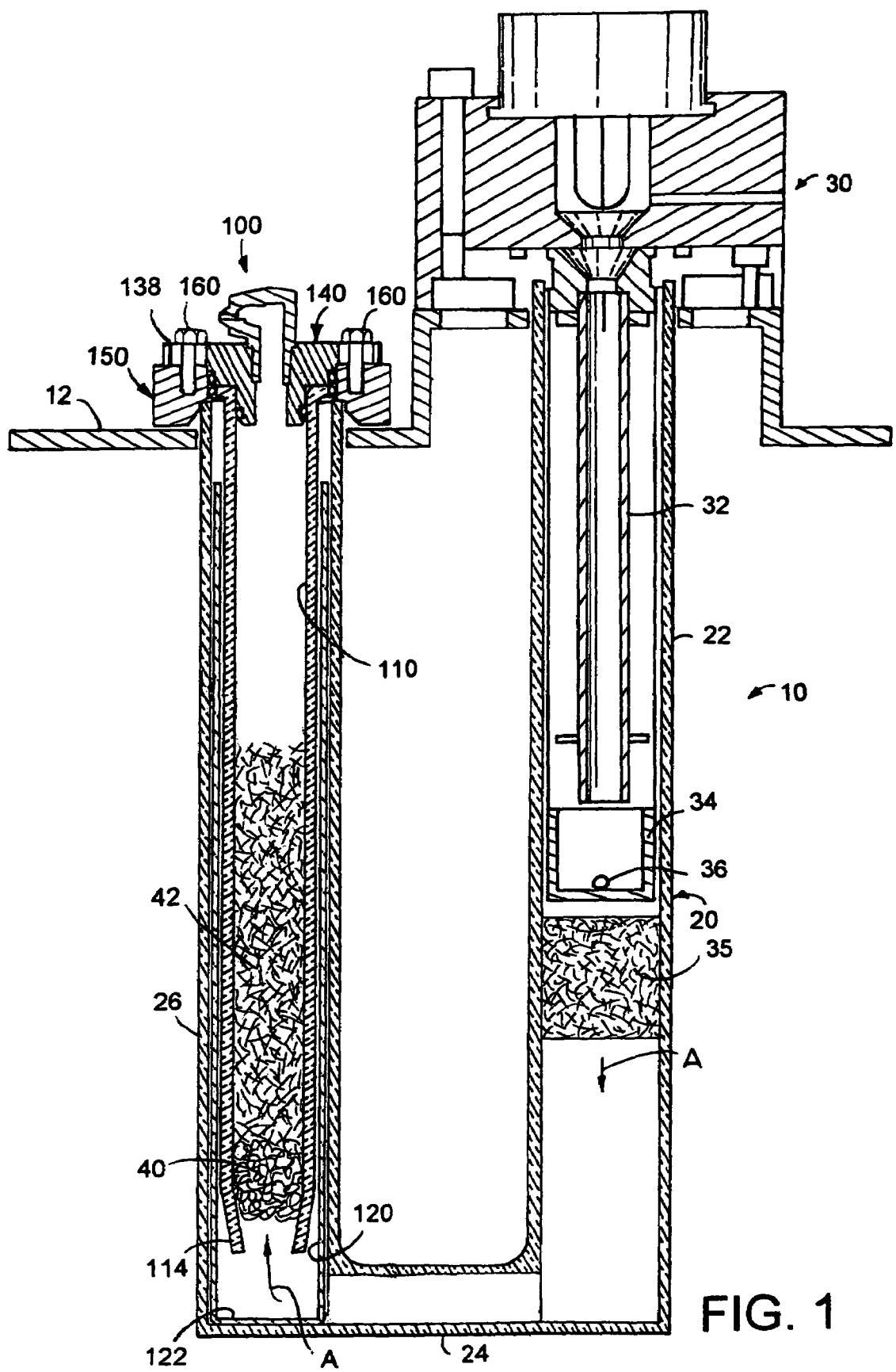
FIG. 1 is a fragmentary cross-sectional view of a resistance combustion furnace and combustion assembly including the reagent assembly of the present invention.

Referring initially to FIG. 1, there is shown an analytical furnace 10 embodying a reagent assembly 100 of the present invention. Furnace 10 is a resistance heating furnace including a generally U-shaped quartz combustion tube 20 having a generally cylindrical vertically extending first or combustion leg 22, a transverse coupling conduit 24, and a vertically upwardly extending second or reagent leg 26. The combustion tube, thus, generally has cylindrical sections 22 and 26 which are joined by the transverse conduit 24. The furnace 10 can generally be of the type disclosed in U.S. Pat. No. 4,622,009, the disclosure of which is incorporated herein by reference, which heats a sample 36 dropped by a sample load assembly 30 of the type disclosed in U.S. Pat. No. 6,291,802, the disclosure of which is incorporated herein by reference, through an oxygen lance and sample introduction tube 32 into a crucible 34. Crucible 34 can be of the type disclosed in U.S. Pat. No. 6,270,727, the disclosure of which is incorporated herein by reference.

Combustion crucible 34 is held in place by a suitable quartz porous plug 35 which allows the byproducts of combustion to flow downwardly through the leg 22 in the direction indicated by arrow A in FIG. 1. The tube 32, in addition to providing a sample drop pathway, serves as an oxygen lance for the introduction of combustion oxygen to the open mouth of the cup-shaped crucible 34 during combustion. The furnace 10 is employed in a micro analysis system in which, after the sample 36 is introduced into the crucible and furnace, which has been heated to approximately 1000° C., a helium carrier gas flows through the combustion chamber 20 until a plug or aliquot of oxygen is introduced through lance 32, for a period of about 5-10 seconds in one embodiment, to complete the combustion of the 1 to 50 mg sample 36 held within crucible 34 to completely combust the sample. The helium carrier gas then carries the byproducts of combustion through the transverse conduit 24 and upwardly, as indicated by arrow A, into the open mouth of the reagent tube 110 of the reagent assembly 100.

Figure 2:
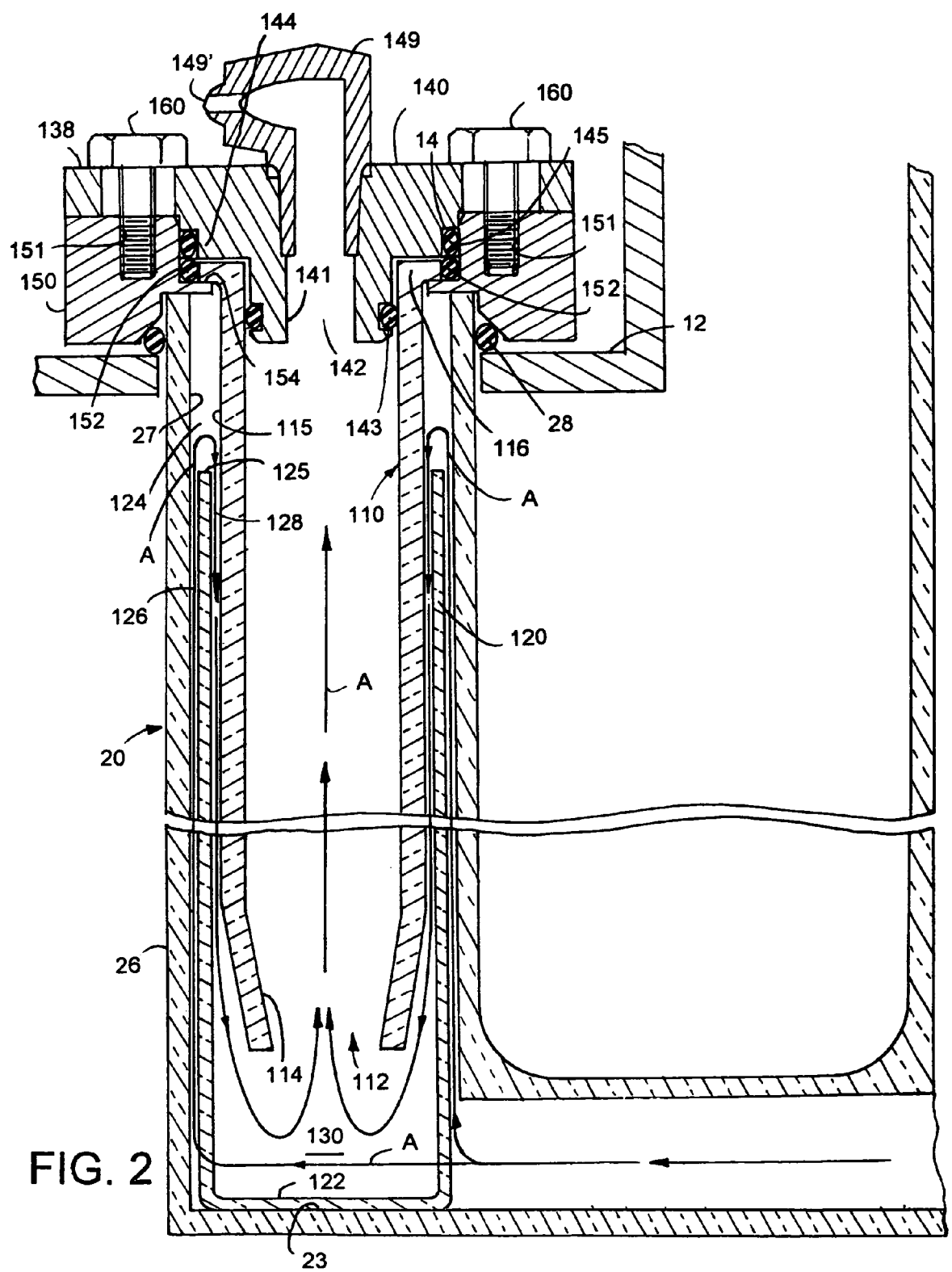
FIG. 2 is an enlarged fragmentary exploded cross-sectional view, partly broken away, of the reagent assembly of the present invention.
Figure 3:
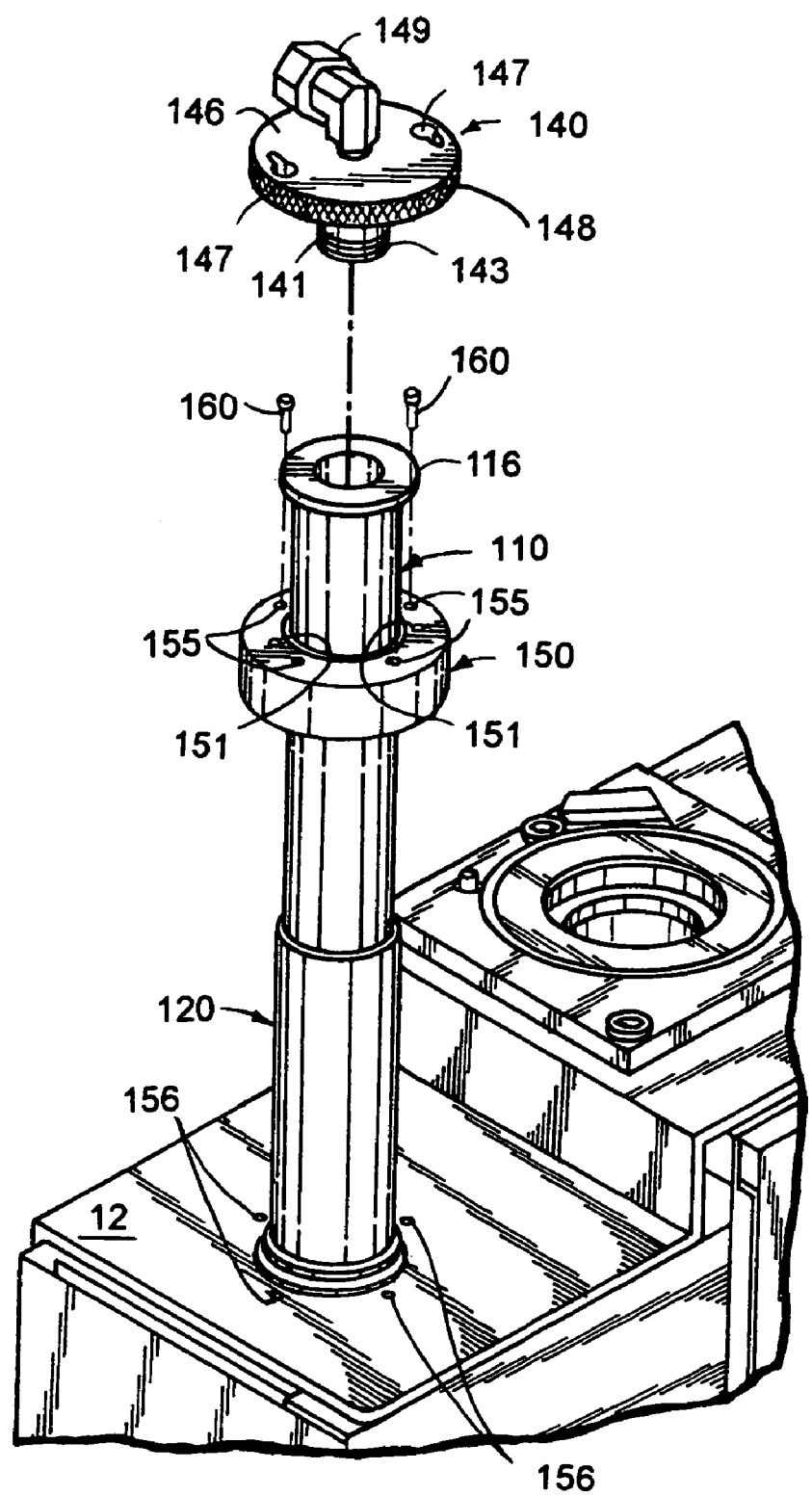
FIG. 3 is an exploded fragmentary perspective view of the combustion furnace and reagent assembly of the present invention.

Reagent tube 110, as seen in FIGS. 1 and 2, is also made of quartz and has an open lower end 112 with an inwardly tapered section 114 holding the reduction reagent 42 in place. Reagent tube 110 is generally cylindrical and includes an annular mounting flange 116 at its open upper end 117 (FIG. 3). Flange 116 rests upon an annular surface 154 of mounting block 150 and is sealed to the mounting block 150 by an O-ring seal 152, as best seen in FIG. 2.

In a preferred embodiment of the invention, the open end 112 of quartz reagent tube 110 had a diameter of about 0.5 inches, while the inner diameter of tube 110 was approximately 0.75 inches, and had a wall thickness of about 3 mm. The outer diameter of tube 110 is approximately 1 inch. The tapered end 114 was tapered at an angle of approximately 20° over a length of approximately 0.70 inches while the overall length of tube 110 was approximately 9.25 inches. The flange 116 has a diameter of 1.2 inches, and tube 110 fits within the circular opening 153 of mounting block 150 with flange 116 engaging the annular surface 154 (FIG. 5) of block 150.

Within the inner removable reagent tube 110, there is packed the reagent comprising in a preferred embodiment, as seen in FIG. 1, copper wool 40 forming a plug at the tapered lower end 114 of the reagent tube 110. Above the copper wool plug 40 there is placed the reduced copper reagent 42 itself comprising finely chopped copper wire sticks which are prepared by placing the sticks in a vacuum furnace with hydrogen to scavenge all the oxygen from the copper. The reagent is commercially available from Leco Corporation of St. Joseph, Mich.

Tube 110 is concentrically and removably mounted within the second leg 26 of combustion tube 20 by a twist-off sealed locking cap 140 removably mounted to mounting block 150, which is affixed to furnace wall 12 as described in greater detail below. Although the reagent tube can be dimensioned to reduce the dead space between its outer diameter and that of the inner diameter of the combustion tube leg 26, in one embodiment, dead space is reduced by the use of an optional second concentric tube 120 as now described.

The generally cylindrical quartz outer tube 120 has a closed lower end or floor 122 which rests on the bottom surface 23 of the leg 26 of combustion tube 20, as best seen in FIG. 2. The quartz tube 120 has a length of about 9 inches and, when resting on the floor of the combustion tube, leg 26 does not extend fully to the top of the reagent tube but rather leaves an open annular space 124 (FIG. 2) above the top edge 125 of tube 120 in the area between the inner wall 27 of combustion tube leg 26 and the outer wall 115 of reagent tube 110.

The outer diameter of the second or outer tube 120 is about 1.18 inches as compared to the inner diameter of 1.25 inches of the combustion tube leg 26, thereby leaving an annular space for the flow of combustion gases in the direction of arrow A around the outer surface of inner tube 120 and the inner surface 27 of combustion tube leg 26 into the annular space 124, which is sealed by an O-ring seal 28 sealing the combustion tube section 26 to the furnace wall 12, as best seen in FIG. 2. The gases, therefore, are forced to flow downwardly in a second annular space 128 between the outer diameter of reagent tube 110 and the inner diameter of outer tube 120. The inner diameter of outer tube 120 is approximately 1.063 inches, such that a gap of approximately 0.0315 inches is formed between the outer wall of the reagent tube 110 and the inner wall of the outer tube 120, allowing the gaseous byproducts of combustion to flow downwardly, as indicated by arrow A, into the open area 130 below open end 112 of tube 110 and above floor 122 of outer tube 120. The gas then flows upwardly as indicated by arrow A through reagents 42 into the exit aperture 142 of removable cap 140.

Figure 4:
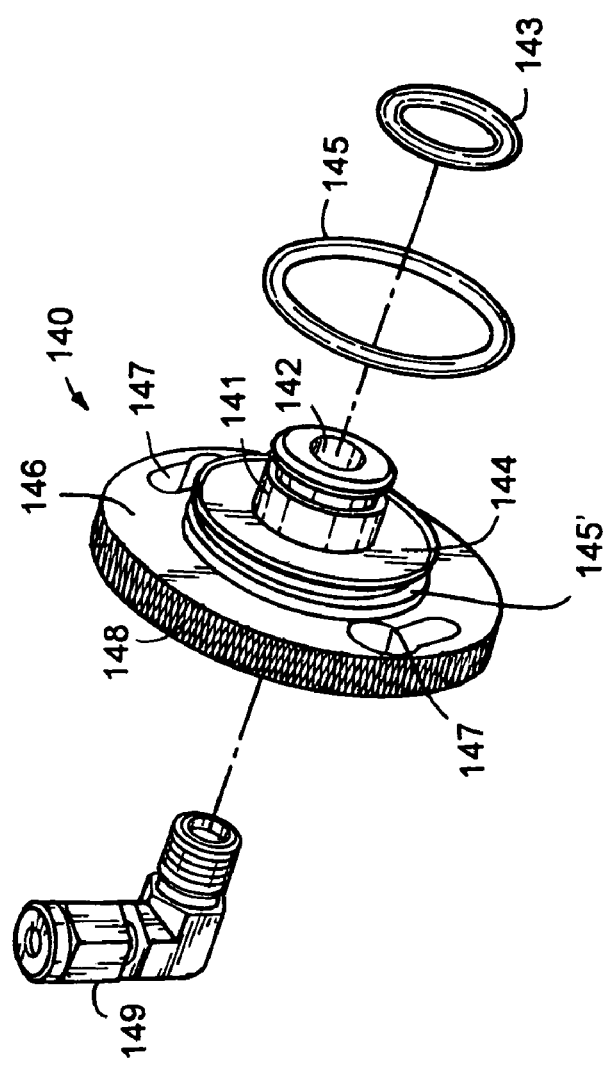
FIG. 4 is an exploded perspective view of the twist-off cap assembly of the reagent assembly of the present invention.

Cap 140 is shown in detail also in the exploded view of FIG. 4 and includes a first cylindrical section 141, which extends downwardly within the open mouth of inner tube 110, as best seen in FIG. 2, and is sealed to the inner surface of tube 110 by sealing O-ring 143. The cap 140 also includes a second, larger diameter annular section 144 which sealably fits within the aperture 153 (FIG. 5) of mounting block 150 and is sealed thereto by an O-ring 145. Cap 140 includes a mounting flange 146 having a diameter greater than that of section 144. Flange 146 includes a pair of keyhole-shaped arcuate slots 147. The outer edge 148 of flange 146 is knurled to allow the cap to twist off from the mounting block 150, which includes a pair of cap bolts 160 over which the cap 140 can be extended and rotated while pressing downwardly to sealably engage the combustion tube section 26 as well as reagent tube 110, which is coupled to cap 140 by the interference fit with O-ring 143 during assembly of the unit. A gas elbow 149 of conventional configuration is threadably coupled to the opposite end of aperture 142 to provide an exit flow path 149' for the byproducts of combustion into the remaining components of the analyzer, as shown in FIG. 6.

Figure 5:
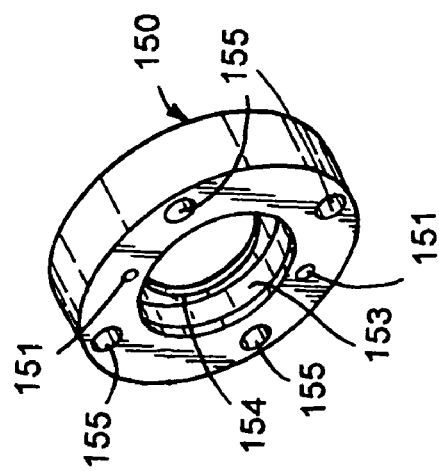
FIG. 5 is a perspective view of the mounting block to which the cap is secured.
Figure 6:
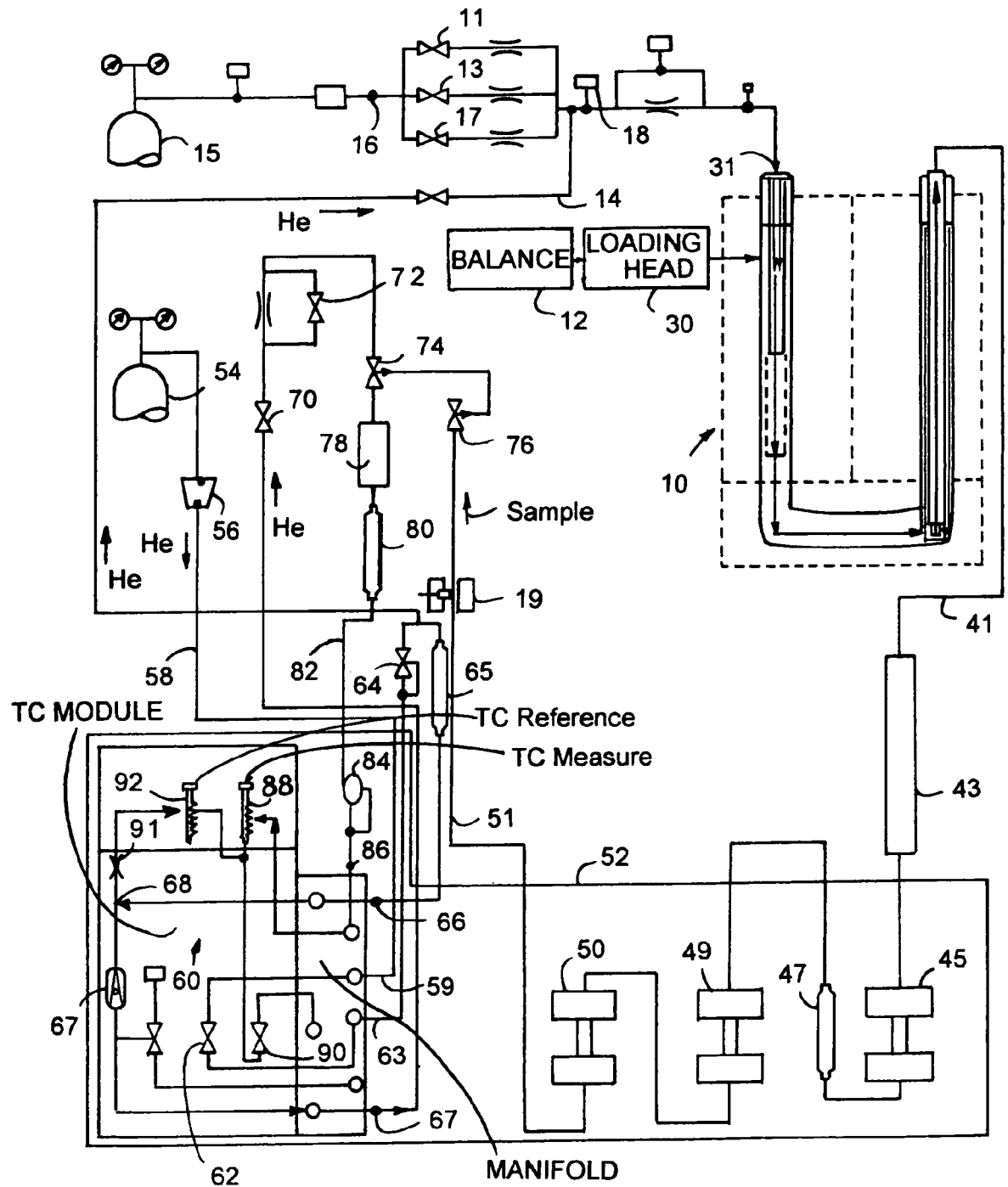
FIG. 6 is a flow diagram of an analyzer embodying the top-loading reagent assembly of the present invention.

Mounting block 150, as seen in FIG. 5, includes blind threaded apertures 151 for receiving the cap bolts 160, which extend upwardly a distance sufficient for extending through slots 147 in flange 146 of the cap 140. Mounting block 150 also includes a plurality of apertures 155 for securing the cap to the furnace wall 12 in a conventional manner in sealed engagement by the use of O-ring 28, as seen in FIG. 2. The details of this mounting arrangement are not shown in the flow path cross-sectional views of FIGS. 1 and 2, however, the furnace wall 12, as seen in FIG. 3, includes threaded apertures 156 for receiving conventional fasteners, such as cap head screws, which extend through apertures 155 in the mounting block 150 for securing mounting block 150 to the furnace wall 12. The cap 140 and mounting block 150 are machined of aluminum or other suitable metal to withstand the pressure and temperature of the byproducts of combustion flowing therethrough. Cap 140 includes an annular recess 145', as seen in FIG. 4, for receiving the sealing O-ring 145, which forms a double seal with the cap and the seal 152 in cap-receiving recess 153 of mounting block 150.

As can be seen in reviewing FIGS. 1-5, the removable reagent tube 110 of assembly 100 allows the furnace 10 to be employed for combusting several samples until the reagent is exhausted. The furnace can be opened to expose the combustion tube and the cap 140 of the removable reagent assembly. Cap 140 is rotated and lifted to gain access to the reagent holding inner tube 110, which can be lifted from the combustion tube reagent section 26 while retaining the outer tube 120 in place to allow the easy replacement of the reagent inner tube 110 either by inserting a freshly made and repacked reagent tube or by cleaning out the existing tube external to the furnace and repacking it with reagent materials 40 and 42. By providing a reagent tube with a flanged upper end and a tapered lower end and having a diameter in cooperation with either the combustion tube leg 26 or the outer tube 120, the flow of byproducts of combustion through the reagent tube is assured, and an easily replaceable reagent section of the combustion system is provided. This greatly reduces the time, effort, and expense required of the prior art systems, where frequently combustion tube 20 itself had to be replaced.

The reagent assembly 100 is initially installed by placing the outer tube 120 within the leg 26 of combustion tube 20, which need not be critically centered in view of the existence of a gap between the outer diameter of reagent tube 110 (or tube 120) and the inner diameter of leg 26 of combustion tube 20, allowing a flow pass of gas therebetween regardless of the precise centering. Similarly, the insertion of reagent tube 110 within the outer tube 120 always allows a generally annular gap therebetween such that the byproducts of combustion will be forced downwardly around the space between the outer or second tube and the reagent tube and then upwardly through the open end of the reagent tube and through the reagent. The overall analyzer, including the unique top-loaded removable reagent assembly 100 of the present invention, is shown in FIG. 6, which is now briefly described.

Inlet 31 (FIG. 6) of furnace 10 receives combustion gas ($O_2$) from a source 15 of oxygen which has a flow rate adjusted between 0.5, 1, 3, 5, or 6 L per minute by the selective activation of parallel flow control valves 11, 13, and 17 in conduit 16 leading from the supply of oxygen to the inlet 31 of the combustion furnace. The $O_2$ pressure is monitored by a pressure sensor 18. The oxygen is jetted into the open mouth of a sample-holding crucible 34 through an oxygen lance 32 to combust the sample. As described above, the byproducts of combustion (i.e., analytes) flow through reagent 42 in reagent tube 110 positioned in leg 26 and from combustion chamber 20 through exit port 149'. Conduit 41 transfers the byproducts of combustion through a heater 43. The byproducts of combustion flowing in conduit 41 then pass through a combustion detector 45 comprising an $H_2O$ IR cell, which detects the hydrogen content in the gas stream as a result of the combustion of the sample 36 in crucible 34. The combustion detector 45 is coupled to a CPU, as described in the above identified '165 publication, for storing the detected hydrogen level.

As seen in FIG. 6, the byproducts of combustion are forced through a flow path including an anhydrone scrubber 47 and an $SO_2$ determining IR cell 49 and a $CO_2$ determining IR cell 50, all contained within a heated chamber 52.

The He carrier gas in conduit 14 then carries the byproducts of combustion through pinch valve 19 in conduit 51 to valve 76. The sample gas then passes through valve 74 into catalytic reduction heater 78 and through anhydrone scrubber 80. Conduit 82 carries the sample gas through a 300 cc/minute flow controller 84 into the nitrogen sample inlet port 86 of thermal conductivity module 60 and through the thermal conductivity measurement device 88, which is coupled to a CPU to provide data relative to the nitrogen concentration detected. After measurement, the gas is then exhausted through an exhaust outlet valve 90. During the measurement of nitrogen concentration by cell 88, He carrier gas at T-junction 68 also flows through a flow restrictor 91 to a thermal conductivity reference cell 92.

He carrier gas from source 54 flows through filter 56 in conduit 58 to inlet port 59 of thermal conductivity module 60 via the actuation of He valve 62. The He gas exits module 60 via port 63, travels through a 12 psi pressure regulator 64 and scrubber 65 into port 66 of thermal conductivity module 60. Heater 78 is filled with copper (Cu) heated to about 750° C. to remove any remaining oxygen and convert NO to free nitrogen ($N_2$), which subsequently flows through the scrubber 80, which includes sodium hydrate silicate for removing $CO_2$ and an anhydrone, which removes water from the gas flow stream.

The control of the valves and the combustion furnace, as well as the measurement and detection of the concentration of gases, is conventionally controlled by a CPU (not shown). The CPU receives an input signal as to the size of the sample from balance 12 and controls the loading head 30 (FIG. 1) to drop the sample within the combustion chamber. The CPU also controls the application of power to furnace 10 through a suitable power control module. The CPU may be coupled to a printer to print the results of the gas concentrations detected. The CPU is programmed in a conventional manner, to analyze the sample based upon standard ASTM standards utilizing data from the infrared detectors and thermal conductivity detectors shown in FIG. 6. As is well known after an analysis cycle, the analyzer is purged to condition it for a subsequent analysis.

It will become apparent to those skilled in the art that various modifications to the preferred embodiment of the invention as described herein can be made without departing from the spirit or scope of the invention as defined by the appended claims.

The invention claimed is:

1. A reagent tube for use in an analytical furnace having a combustion tube with a generally cylindrical section, said reagent tube comprising:
  a cylindrical member having an inner and an outer diameter and a first open end which defines an opening smaller in diameter than said inner diameter of said cylindrical member, said cylindrical member including a second open end opposite said first end, wherein said outer diameter of said reagent tube allows its insertion into the combustion tube, and said cylindrical member including an annular mounting flange at said second end.

2. The reagent tube as defined in claim 1 wherein said first open end is inwardly tapered to reduce the diameter of said opening.

3. The reagent tube as defined in claim 2 wherein said cylindrical member is made of quartz.

4. The reagent tube as defined in claim 3 and further including a reagent packed into said cylindrical member.

5. The reagent tube as defined in claim 4 wherein said reagent comprises copper wire fragments.

6. A quartz reagent tube for use in an analytical furnace having a generally U-shaped combustion tube, said reagent tube comprising:
  a cylindrical tube made of quartz having a first open end which is inwardly tapered to define a circular opening smaller in diameter than the diameter of said cylindrical tube, said cylindrical tube including a mounting flange at a second end opposite said first end, wherein the outer diameter of said reagent tube allows its insertion into one leg of the combustion tube; and
  a reagent packed into said reagent tube.

7. A reagent assembly for use in a combustion furnace for an elemental analyzer for receiving and combusting samples for analysis, said combustion furnace including a combustion tube for receiving a combustion crucible and a reagent assembly including a reagent tube for holding a reagent therein, said reagent tube comprising: a cylindrical member having an inner and an outer diameter and a first open end which defines an opening smaller in diameter than said inner diameter of said cylindrical member, said cylindrical member including a second open end opposite said first end, wherein said outer diameter of said reagent tube allows its insertion into the combustion tube, and said cylindrical member including an annular mounting flange at said second end.

8. The apparatus as defined in claim 7 wherein said combustion tube is cylindrical and said reagent tube is generally cylindrical and has a first open end which is inwardly tapered for holding a reagent in said tube.

9. The apparatus as defined in claim 8 wherein said reagent assembly further includes a cap sealably coupled to said reagent tube, said cap having a gas outlet.

10. The apparatus as defined in claim 9 and further including a mounting block sealably coupled to said combustion tube and sealably coupled to said cap, said mounting block includes at least one fastener and said cap includes at least one slotted aperture for removably securing said cap to said combustion furnace.

11. The apparatus as defined in claim 10 wherein said combustion tube is generally U-shaped and has a first leg for receiving a combustion crucible, a second leg for receiving said reagent tube, and a section coupling said first and second legs.

12. The apparatus as defined in claim 11 wherein said reagent assembly further includes a second tube positioned in said second leg of said combustion tube between said reagent tube and said combustion tube to force byproducts of combustion through said reagent tube.

13. The apparatus as defined in claim 12 wherein said second tube is generally cylindrical having an enclosed end and an inner diameter for receiving said reagent tube such that a gas flow path exists between the inner diameter of said second tube and the outer diameter of said reagent tube.

14. The apparatus as defined in claim 13 wherein said combustion tube, said reagent tube, and said second tube are made of quartz.

15. A reagent assembly for use in an elemental analyzer for detecting chemical elements in gaseous byproducts of combustion including a combustion furnace for receiving samples for combustion, said combustion furnace including a generally U-shaped combustion tube having a first leg for receiving a sample-receiving combustion crucible and a second leg coupled to said first leg for receiving a reagent, said reagent assembly comprising: a reagent tube for holding a reagent, said reagent tube removably inserted into said second leg of said combustion tube, wherein said reagent tube comprises a cylindrical member having an inner and an outer diameter and a first open end which defines an opening smaller in diameter than said inner diameter of said cylindrical member, said cylindrical member including a second open end opposite said first end, wherein said outer diameter of said reagent tube allows its insertion into the combustion tube, and said cylindrical member including annular mounting flange at said second end.

16. The apparatus as defined in claim 15 wherein said reagent tube is generally cylindrical and has a first open end which is inwardly tapered for holding a reagent in said tube.

17. The apparatus as defined in claim 16 wherein said reagent assembly further includes a cap removably coupled to said combustion tube and sealably coupled to said reagent tube, said cap having a gas outlet.

18. The apparatus as defined in claim 17 and further including a mounting block sealably coupled to said combustion furnace and to said combustion tube and further sealably coupled to said cap, said mounting block including at least one fastener for removably securing said cap to said mounting block.

19. The apparatus as defined in claim 18 wherein said reagent assembly includes a second tube positioned in said second leg of said combustion tube and configured to force byproducts of combustion through said reagent tube.

20. The apparatus as defined in claim 19 wherein said second tube is generally cylindrical having an enclosed end and an inner diameter for receiving said reagent tube such that a gas flow path exists between the inner diameter of said second tube and the outer diameter of said reagent tube.

* * * * *